(12) United States Patent
Rudolf et al.

(10) Patent No.: US 9,249,215 B2
(45) Date of Patent: Feb. 2, 2016

(54) HUMAN MONOCLONAL ANTIBODY AGAINST S. AUREUS DERIVED ALPHA-TOXIN AND ITS USE IN TREATING OR PREVENTING ABSCESS FORMATION

(75) Inventors: Michael Rudolf, Ittigen (CH); Holger Koch, Zürich (CH)

(73) Assignee: Aridis Pharmaceuticals, Inc., San Jose, CA (US)

( * ) Notice: Subject to any disclaimer, the term of this patent is extended or adjusted under 35 U.S.C. 154(b) by 202 days.

(21) Appl. No.: 13/388,254

(22) PCT Filed: Aug. 10, 2010

(86) PCT No.: PCT/EP2010/004884
§ 371 (c)(1),
(2), (4) Date: Apr. 16, 2012

(87) PCT Pub. No.: WO2011/018208
PCT Pub. Date: Feb. 17, 2011

(65) Prior Publication Data
US 2012/0201829 A1    Aug. 9, 2012

Related U.S. Application Data

(60) Provisional application No. 61/266,330, filed on Dec. 3, 2009.

(30) Foreign Application Priority Data

Aug. 10, 2009   (EP) .................................... 09010311

(51) Int. Cl.
| | | |
|---|---|---|
| C07K 16/00 | (2006.01) | |
| C12P 21/08 | (2006.01) | |
| C12N 5/04 | (2006.01) | |
| A61K 39/40 | (2006.01) | |
| C12N 5/07 | (2010.01) | |
| C12N 5/16 | (2006.01) | |
| C12P 21/04 | (2006.01) | |
| C12N 1/00 | (2006.01) | |
| C07K 16/12 | (2006.01) | |
| A61K 39/00 | (2006.01) | |

(52) U.S. Cl.
CPC ....... *C07K 16/1271* (2013.01); *A61K 2039/505* (2013.01); *C07K 2316/96* (2013.01); *C07K 2317/56* (2013.01); *C07K 2317/565* (2013.01)

(58) Field of Classification Search
None
See application file for complete search history.

(56) References Cited

FOREIGN PATENT DOCUMENTS

| | | |
|---|---|---|
| WO | WO2007/141274 | 12/2007 |
| WO | WO2007/145689 | 12/2007 |
| WO | WO 2007/145689 A1 | 12/2007 |

OTHER PUBLICATIONS

Abbas et al. Cellular and Molecular Immunology 4th edition, 2000 Chapter 48 p. 42-43 and p. 48.*
Paul, Fundamental Immunology, 3rd Edition, 1993, pp. 292-295.*
Brown et al. J Immunol. May 1996; 156(9):3285-91.*
Bendig et al. Methods: A Companion to Methods in Enzymology 1995.*
Heveker et al. Hum. Antibod. Hybridomas, 1994, vol. 4, 1 and 2, p. 18-24.*
Harshman et al. Toxicon, vol. 24, issue 4, 1986, pp. 403-411.*
DePascalis. J. Immunol. 169:3076-3084, 2002.*
Rudikoff et al. PNAS 79:1979-1983, 1982.*
Chen et al. Protein Engineering (1999) 12(4): 349-356).*
Chen et al. J. Exp. Med 176:855-866 1992.*
Vadjos et al. J. Mol. Biol, 2002, 320:415-428.*
Soderquist, et al., "Enzyme immunoassay for detection of alpha-toxin from *Staphylococcus aureus*" 1993, Serodiagn. Immunother. Infect Disease 5(1):23-26.
Blomqvist, et al., "Production and Characterization of monoclonal Antibodies Against *Staphylococcus aureus* alpha-toxin" 1988 Toxicon 26(3):265-273.
Menzies, et al., "Passive Immunization with Antiserum to a Nontoxic Alpha-Toxin Mutant from *Staphylococcus aureus* Is Protective in a Murine Model." 1996, Infection and Immunity 64(5):1839-1841.
Wardenburg, et al., "Vaccine protection against *Staphylococcus aureus* pneumonia." 2008, Journal of Experimental Medicine 205(2):287-294.
European Search Report dated Dec. 17, 2009 for European Application No. 09010311.0.
International Search Report dated Sep. 21, 2010 for International Application No. PCT/EP2010/004884.
Baderas et al., "Affinity Maturation of Antibodies Assisted by in Silico Modeling." 2008, *PNAS*, 105(26): 9029-9034.
De Pascalis et al., "In Vitro Affinity Maturation of a Specificity-Determining Region-Grafted Humanized Anticarcinoma Antibody: isolation and Characterization of Minimally Immunogenic High-Affinity Variants." 2003, *Clin Cancer Res*, 9: 55521-5531.
Levine et al., "New Knowledge on Pathogenesis of Bacterial Enteric Infections as Applied to Vaccine Development." 1983, *Microbiological Reviews*, 47(4):510-550.

(Continued)

*Primary Examiner* — Oluwatosin Ogunbiyi
(74) *Attorney, Agent, or Firm* — Gary Baker; Quine Intellectual Property Law Group, P.C.

(57) ABSTRACT

The present invention includes a human monoclonal antibody specific for the alpha-toxin of *S. aureus*, a hybridoma producing it, nucleic acids encoding it, and host cells transfected therewith. Further, the present invention includes methods for producing the monoclonal antibody. In addition, the present invention includes pharmaceutical compositions comprising at least one antibody or at least one nucleic acid encoding the antibody. Further, the present invention includes the use of the monoclonal antibody for treating or preventing abscess formation.

17 Claims, 7 Drawing Sheets

(56) References Cited

OTHER PUBLICATIONS

Rauch et al., "Abscess Formation and Alpha-Hemolysin Induced Toxicity in a Mouse Model of *Staphylococcus aureus* Peritoneal Infection." 2012, *Infection and Immunity*, 80(10): 3721-3732.
Wesolowski et al., "Single Domain Antibodies: Promising Experimental and Therapeutic Tools in Infection and Immunity." 2009. *Med Microbiol Immunol*, 198: 157-174.
Winkler et al., "Changing the Antigen Binding specificity by Single Point Mutations of an Anti-p24 (HIV-1) Antibody." 2000, *The Journal of Immunology*, 165: 4505-4514.
Adlam, et al. (1977) "Effect of immunization with highly purified alpha- and beta-toxins on staphylococcal mastitis in rabbits." *Infection and Immunity*, 17(2): 250-256.

* cited by examiner

GAG GTG CAG ATG GTG CAG TCT GGA GCA GAG GTG AAA AAG CCG GGG GAA CCT CTG AAG
Glu Val Gln Met Val Gln Ser Gly Ala Glu Val Lys Lys Pro Gly Glu Pro Leu Lys

ATC TCC TGT AAG GGT TCT GGA TAC AAG TTT GGC ACC CAC TGG ATC GGC TGG GTG CGC
Ile Ser Cys Lys Gly Ser Gly Tyr Lys Phe Gly Thr His Trp Ile Gly Trp Val Arg
                                          CDR1

CAG AGG CCC GGG AAA GGC CTG GAG TGG ATG GGA ATC ATC CAT CCT GCT GAC TCT GAA
Gln Arg Pro Gly Lys Gly Leu Glu Trp Met Gly Ile Ile His Pro Ala Asp Ser Glu
                                                            CDR2

ACC AAG TAC AGC CCG TCA TTC CAA GGC CAG GTC TCT TTC TCA GCC GAC AAG TCC AGC
Thr Lys Tyr Ser Pro Ser Phe Gln Gly Gln Val Ser Phe Ser Ala Asp Lys Ser Ser

AAT ACC GCC TAC CTA CAT TGG AGC ACC CTG AGG GCC TCG GAC ACC GCC ATG TAT TAC
Asn Thr Ala Tyr Leu His Trp Ser Thr Leu Arg Ala Ser Asp Thr Ala Met Tyr Tyr

TGT GCG AGA CGA TCT GGG AGC AGC AGT TGG TAT GCT CTT GAT TTC TGG GGC CAA GGG
Cys Ala Arg Arg Ser Gly Ser Ser Ser Trp Tyr Ala Leu Asp Phe Trp Gly Gln Gly
                        CDR3

ACA ATG GTC ACC GTC TCT TCA GCC TCC ACC AAG GGC CCA TCC GTC
Thr Met Val Thr Val Ser Ser Ala Ser Thr Lys Gly Pro Ser Val

```
CAG TCT GTG CTG ACT CAG TCA CCC TCA GCG TCG GGG ACC CCC GGG CAG AGG GTC ACC
Gln Ser Val Leu Thr Gln Ser Pro Ser Ala Ser Gly Thr Pro Gly Gln Arg Val Thr

ATC TCT TGT TCT GGA GGC AGC TCC AAC ATC GGA AGT AAT ACT GTA AAT TGG TAC CAA
Ile Ser Cys Ser Gly Gly Ser Ser Asn Ile Gly Ser Asn Thr Val Asn Trp Tyr Gln
                              CDR1

CAG TTC CCA GGA GCG GCC CCC AAA CTC CTC ATC TAT ACT AAT AAT CAG CGG CCC TCA
Gln Phe Pro Gly Ala Ala Pro Lys Leu Leu Ile Tyr Thr Asn Asn Gln Arg Pro Ser
                                                      CDR2

GGG GTC CCT GAC CGA TTC TCT GGC TCC AAG TCT GGC ACC TCA GCC TCC CTG GCC ATC
Gly Val Pro Asp Arg Phe Ser Gly Ser Lys Ser Gly Thr Ser Ala Ser Leu Ala Ile

AGT GGG CTC CAG TCT GAG GAT GAG GCT GAT TAT TAC TGT GCA ACA TGG GAT GAC AGC
Ser Gly Leu Gln Ser Glu Asp Glu Ala Asp Tyr Tyr Cys Ala Thr Trp Asp Asp Ser
                                                          CDR3

CTA AAT GGC CTT TAC GTC TTC GGA ACT GGG ACC AAG GTC ACC GTC CTA GGT CAG CCC
Leu Asn Gly Leu Tyr Val Phe Gly Thr Gly Thr Lys Val Thr Val Leu Gly Gln Pro
     CDR3

AAG GCC AAC CCC ACT GTC ACT CTG TTC
Lys Ala Asn Pro Thr Val Thr Leu Phe
```

HUMAN MONOCLONAL ANTIBODY AGAINST *S. AUREUS* DERIVED ALPHA-TOXIN AND ITS USE IN TREATING OR PREVENTING ABSCESS FORMATION

CROSS-REFERENCE TO RELATED APPLICATION

The present application is a 35 U.S.C. §371 national phase application from, and claiming priority to, International Application No. PCT/EP2010/004884, filed Aug. 10, 2010, and published under PCT Article 21(2) in English, which claims priority to European Patent Application No. 09 010 311.0, filed Aug. 10, 2009, and U.S. Provisional Patent Application No. 61/266,330, filed Dec. 3, 2009, which applications are incorporated by reference herein in their entireties.

FIELD OF THE INVENTION

The present invention relates to a human monoclonal antibody specific for the alpha-toxin of *S. aureus*, a hybridoma producing it, nucleic acids encoding it, and host cells transfected therewith. Further, the present invention relates to methods for producing said monoclonal antibody. In addition, the present invention relates to pharmaceutical compositions comprising at least one antibody or at least one nucleic acid encoding said antibody. Further, the present invention relates to the use of said monoclonal antibody for treating or preventing abscess formation.

BACKGROUND OF THE INVENTION

*Staphylococcus aureus* (*S. aureus*) is a facultative anaerobic, gram positive, spherical bacterium considered to be an opportunistic pathogen. *S. aureus* commonly colonizes the nose, skin and mucosal surfaces of the gastrointestinal tract of healthy humans. Approximately 20-30% of the population is colonized with *S. aureus* at any given time. These bacteria often cause minor infections, such as pimples and boils in healthy individuals. Normally, mucosal and epidermal barriers (skin) protect against *S. aureus* infections. Interruption of these natural barriers as a result of injuries—such as burns, trauma or surgical procedures—dramatically increases the risk of infection and could cause severe and/or systemic infections. Diseases that compromise the immune system (e.g., diabetes, end-stage renal disease, cancer, AIDS and other viral infections), but also immunosuppressive therapies—e.g. as radiation, chemotherapeutic and transplantation therapies-increase the risk of infection. Opportunistic *S. aureus* infections can become quite serious, causing endocarditis, bacteremia, osteomyelitis and abscess formation, which might result in severe morbidity or mortality. *S. aureus* infections may be divided in localized infection, such as pneumonia, and clinically more complex *S. aureus* infections, such as blood stream infections and abscess formation caused by distant organ seeding.

*S. aureus* is a leading cause of bloodstream, skin, soft tissue, and lower respiratory tract infections worldwide. The frequencies of both nosocomial and community-acquired infections have increased steadily over the years. In addition, treatment of these infections has become more challenging due to the emergence of multi-drug resistant strains. In developed countries such as the United States, resistance to β-lactam antibiotics in methicillin-resistant *S. aureus* strains (MRSA) is a major problem in hospitals and other healthcare settings. Notably, the incidence rate of all invasive MRSA infections, including those outside of hospitals, is high compared with other bacterial pathogens and 20% of these infections result in death. In addition the occurrence of acquired resistance to vancomycin further limited the treatment options for severe *S. aureus* infections.

*S. aureus* has a diverse arsenal of virulence factors that contribute to the pathogenesis of disease. These can be broadly subdivided into surface and extracellular secreted proteins. Surface proteins include both structural components of the bacterial cell wall, such as peptidoglycan and lipoteichoic acid, and surface proteins preferentially expressed during exponential growth, including protein A, fibronectin-binding protein and clumping factor. Secreted proteins are generally expelled from the bacterial cells during the stationary phase of bacterial growth and include several toxins such as alpha-toxin (also known as hemolysin alpha), enterotoxin B, leukocidins (including Panton-Valentine Leukocidine PVL), lipase and V8 protease. Yet despite the broad knowledge about the biochemical and molecular properties of these toxins, the precise role of the toxins in the pathogenesis of *S. aureus* infections is not entirely understood.

Experimental evidence and epidemiological data have suggested that amongst other cytotoxins, alpha-toxin may be involved in the pathogenesis of pneumonia (Mc Elroy et al, 1999). Alpha-toxin is thought to engage surface receptors of sensitive host cells and thus attaching to the cell surface. This event promotes toxin oligomerization into a heptameric pre-pore and insertion of a β-barrel structure with a 2-nm pore diameter into the plasma membrane. The formation of the pore is causing loss of membrane integrity, destabilizing the cells and ultimately leading to apoptosis and cell lysis. In particular lymphocytes, macrophages, alveolar epithelial cells, pulmonary endothelium, and erythrocytes are sensitive to pore formation by alpha-toxin; however, granulocytes and fibroblasts appear resistant to lysis (McElroy et al., 1999).

The exact role of alpha-toxin in the inflammatory response and the induction of innate immune response to bacterial infections are not fully understood. *S. aureus* expresses a number of other virulence factors and to date the contribution of each virulence factor to disease manifestation is not fully understood and poses a challenge to the development of prophylaxis and therapy of clinically complex *S. aureus* infection.

Alpha-toxin is known to be one of the virulence factors for the establishment of *S. aureus* infections in the host and a number of studies have highlighted the importance of alpha-toxin in disease. e.g. instillation of purified alpha-toxin into rabbit or rat lung tissue triggers vascular leakage and pulmonary hypertension, which has been attributed to the release of different signaling molecules (e.g., phosphatidyl inositol, nitric oxide, prostanoids, and thromboxane $A_2$). In the literature it has been shown that anti-alpha-toxin immunity is protective against the toxin's detrimental effects, but designing vaccines against alpha-toxin remains a significant challenge.

Wardenburg and Schneewind (2008) demonstrated that the severity of lung disease in mice correlates with the levels of alpha-toxin produced by a particular *S. aureus* isolate. Furthermore the authors showed that immunization against a nonpore-forming alpha-toxin variant induced immunity to pneumonia caused by *S. aureus*. These findings are consistent with a study from the same group demonstrating that alpha-toxin is important for the pathogenesis of CA-MRSA pneumonia (community-associated methicillin-resistant *S. aureus*). In another setting the authors demonstrated that antibodies against alpha-toxin also protected human lung epithelial cells from *S. aureus*-induced lysis (Wardenburg and Schneewind (2008)).

Although these results indicate that alpha-toxin contributes to lung tissue destruction, it is not yet clear whether the animals' death in the above described experiments resulted from direct destruction of lung cells by the toxin, from an excessive inflammatory response, or from both. Passive transfer of alpha-toxin antibodies significantly reduced circulating levels of interleukin 1β, a cytokine known to accompany acute lung injury. Therefore, it is reasonable to conclude that the inflammatory response may contribute to alpha-toxin-mediated lung damage.

During a localized infection such as pneumonia in humans, approx. 40% of patients with *S. aureus* pneumonia develop blood stream infections and disseminated disease. The dissemination of the bacterial infection can lead to blood stream infection and distant organ seeding. The blood stream infection can lead to septicemia, a rapidly progressing and frequently fatal complication of *S. aureus* infections.

The dissemination of an *S. aureus* infection is also commonly seen in *S. aureus* pneumonia animal models, again with approximately 40% of animal developing disseminated bacteremia due to tissue damage and spreading of the infection through epithelial layers into the blood stream and lymphatic tissue. Nevertheless the dissemination largely depends on the genetic background of the animal strain used and the potential of the innate immune system, such as neutrophil activation, to control the growth. e.g. neutrophil depleted C57B/L animals are highly susceptible to kidney infections with *S. aureus* whereas immune competent animals are resistant to infections. In contrast A/J animals were very susceptible, mainly due to delayed recruitment of neutrophils to the kidney (von Köckritz-Blickwede, 2008).

Although data on structure and function of *S. aureus* proteins became more comprehensive the development of an effective vaccine remains a challenge.

An attempt was made to safely confer immunity to alpha-toxin and *S. aureus* bacteria by the use of compositions comprising a combination of antibodies that specifically bind to an *S. aureus* alpha-toxin antigen and antibodies that specifically bind to another bacterial antigen (WO 2007/145689). These compositions, while comprising amounts of antibody that are not effective on their own, nevertheless neutralize infection and/or provide protection against infection by the synergistic activity of the combination of antibodies.

The protective efficacy of said combination of *S. aureus* toxin-neutralizing and opsonic antibodies at 72 hours post-bacterial challenge with a *S. aureus* isolate is demonstrated as compared to the protective effect of immunization with either neutralizing or opsonic antibodies alone. The combination of the opsonic and toxin-neutralizing antibodies demonstrated a protective effect in preventing skin and soft tissue infection and organ seeding. However, the neutralizing anti-alpha-toxin antibody disclosed by that patent application itself is not sufficient to prevent organ seeding/abscess formation or to neutralize infection.

A further attempt was made by Heveker et al (1994a, 1994b) that describes neutralizing human and murine monoclonal antibodies directed against *S. aureus* alpha-toxin. The human monoclonal antibody of IgG/lambda subtype is characterized by sequence and shows neutralization.

The anti-alpha toxin antibody producing human hybridoma described by Heveker (1994a) was isolated using peripheral blood leukocytes from a healthy volunteer previously immunized with a *S. aureus* alpha toxoid test vaccine. While the alpha-toxoid used in the Heveker study represents a chemically modified alpha-toxin it could be assumed that the modification does render antigenic determinants less immunogenic or even non-immunogenic and as such the approach could not produce equally effective immunity, as was demonstrated for other bacterial toxins, such as cholera toxin, where toxoid vaccines stimulated anti-toxin antibodies which did not confer immunity to infections (Levine (1983)).

Various factors have been identified in the literature as critical virulence factors for abscess formation, such as toxins, peptidoglycans, extracellular factors and enzymes. A potential role of alpha-toxin in the formation of abscesses was postulated by Kapral et al. (1980). Alpha-toxin is reported to dramatically accumulate in the abscess upon maturation of abscesses although it could not be demonstrated that alpha-toxin is necessary for the abscess formation. A second publication by Adlam et al (1977) negated a key role in the abscess formation for alpha-toxins. The authors demonstrated that alpha-toxin plays a key role in the spreading hemorrhagic form of rabbit mastitis blue-breast seen in natural outbreaks. They reproduced the clinical picture in the laboratory with two unrelated *staphylococcal* strains. A high circulating anti-alpha-toxin-titer conferred protection against this lethal form of mastitis. Thus, the neutralizing titer could prevent fatal outcome by modifying the clinical picture to the less severe abscess condition. However, neutralization of alpha-toxin did not affect/prevent abscess formation in rabbits. In a more recent publication Kielian et al (2001) investigated the role of alpha-toxin in brain abscess formation in a mouse model. Experimentally the authors implanted wild type *S. aureus* strains and mutants thereof into the frontal lobe brain tissue and evaluated the ability to induce brain abscesses of each strain. The authors used strains mutant in loci relevant for expression of known virulence factors, e.g. mutants in the sarA locus and the agr locus, both involved in the global regulation of important virulence factors. As alpha-toxin is under control of the sarA/agr regulatory system, the authors also included an alpha-toxin mutant strain into their experiments. The experimental data demonstrated that the replication of mutant bacterial strains for alpha-toxin or the sarA/agr locus had reduced virulence upon injection of bacterial cells into the skull compared to its isogenic control strain RN6390, resulting in lower bacterial numbers and small inflammatory foci in the brains of animals to be detected, as compared to the large well-formed abscesses in those mice receiving the isogenic strain.

However, the mutant strains were not entirely avirulent in the experimental brain abscess model and it cannot be ruled out that additional factor(s) besides alpha-toxin play critical role(s) in brain abscess formation.

The role of alpha-toxin in the abscess formation was evaluated in another experimental setting as outlined by Schwan et al (2003) in an analysis of local, systemic and abscess forming *S. aureus* infection models. The authors noted that non-hemolytic *S. aureus* strains became more abundant as time passed in murine abscess and wound models, but not within organ tissues associated with systemic infections. E.g. in a mixed infection using all variants of *S. aureus* strain RN6390 (hyperhemolytic, hemolytic, and nonhemolytic) in the abscess model, the hyperhemolytic group markedly declined at day 7 post infection, whereas the nonhemolytic population increased significantly. Sequencing of several of the signature-tagged mutants indicated mutations in the agrC gene or within the agrA-agrC intergenic region, which resulted in curtailing both the alpha-toxin and delta-toxin activity. Analyzing specific mutant strains for agr activity (agr-) and alpha-toxin (hla-) in abscess, wound and systemic models of infection, the agr-mutant strain and the hla-mutant strain showed no difference in bacterial counts in murine abscesses at day 4 as compared to the parental wild type strains (RN6390). The same held true for local infections (wound model), whereas considerable clearing of the hla mutant strain and the agr mutant strain occurred in the systemic model of infection. The result clearly indicated the importance of alpha-toxin in systemic infections but not in local infections or abscess formation. In fact mixed infections with the hla-mutant and wild type strains in the abscess model showed a slight advantage given to the hla mutant population over the wild type strain. The authors even concluded that the agr mutations cause reductions in the expression of alpha- and delta-toxins, which in turn contributed to a growth advantage of this agr mutant group within a mixed population of S. aureus cells residing in abscesses and wounds. The results apparently contradict the results described by Kielian et al, where the lack of alpha-toxin production reduced bacterial virulence. Therefore the role of alpha-toxin in abscess formation is not clear.

Overall there is no evidence pointing to one single virulence factor as the main driver in abscess formation. As such research focused on the presence of additional factors not entirely controlled by S. aureus, such as environmental factors, or given structural motifs as the common key factor in abscess formation. E.g. the most recent data regarding virulence factors affecting the formation of abscesses points to the effects of unchelated bivalent metal ions, such as $Mn^{++}$ and $Ca^{++}$ on abscess formation and bacterial growth within abscesses. Chelation of metal ions in animals inhibited the formation of liver abscesses and inhibited growth of S. aureus in abscesses (Corbin 2008). On the other hand Tzianabos et al. (2001) hypothesized that an organism such as S. aureus requires virulence factors present on the bacterial cell in order to establish pathological structures such as abscesses in tissue. They demonstrated that strains highly associated with clinical cases of abscesses may possess one or more cell wall-associated polysaccharides with a zwitterionic charge motif (a chemical compound that carries a total net charge of 0, thus electrically neutral but carries formal positive and negative charges on different atoms). In the absence of the zwitterionic charge motif no abscess formation could be observed. The authors concluded that these polysaccharide polymers may modulate abscess induction by this organism. In addition they presented confirming data for not only the core polysaccharides CP5 and CP8 but also for the lipoteichoic acid (LTA), an additional well characterized virulence factor within the cell wall. They identified a zwitterionic charge motif within the LTA as well and therefore generalized their hypothesis for abscess formation to the presence of a zwitterionic charge motif in any pivotal virulence factor for the abscess formation.

Based on the results indicating that various factors contribute to S. aureus mediated abscess formation, a person skilled in the art would not expect that neutralization of a single factor would prevent abscess formation.

BRIEF SUMMARY OF THE INVENTION

Thus, an object of the invention is the provision of means and methods for prophylaxis and therapy of clinically complex S. aureus infection, such as abscess formation.

Accordingly, one technical problem underlying the present invention is to provide a monoclonal antibody specific to alpha-toxin derived from S. aureus, wherein the antibody has protective capacity in vivo, against clinically complex S. aureus infection, such as abscess formation.

The technical problem is solved by the monoclonal antibodies as defined in the following.

The present invention provides a monoclonal antibody termed 243-4 specific for alpha-toxin of S. aureus, wherein the variable region of the light chain of the antibody comprises at least one of SEQ ID NO:1 in the CDR1 region, SEQ ID NO:2 in the CDR2 region and SEQ ID NO:3 in the CDR3 region, and wherein the variable region of the heavy chain of the antibody comprises at least one of SEQ ID NO:4 in the CDR1 region, SEQ ID NO:5 in the CDR2 region and SEQ ID NO:6 in the CDR3 region, or a fragment or mutein thereof capable of binding alpha-toxin of the S. aureus, wherein the mutein of the monoclonal antibody carries at least one conservative substitution in any one of the CDR regions in the heavy or light chain.

According to a preferred embodiment of the present invention, a human monoclonal antibody, specific for alpha-toxin of S. aureus is provided wherein the variable region of the light chain of the antibody comprises SEQ ID NO:1 in the CDR1 region, SEQ ID NO: 2 in the CDR2 region and SEQ ID NO:3 in the CDR3 region, and wherein the variable region of the heavy chain of the antibody comprises SEQ ID NO:4 in the CDR1 region, SEQ ID NO:5 in the CDR2 region and SEQ ID NO:6 in the CDR3 region; or a fragment or mutein thereof capable of binding alpha-toxin of the S. aureus, wherein the mutein of the monoclonal antibody carries at least one conservative substitution in any one of the CDR regions in the heavy or light chain.

DETAILED DESCRIPTION OF THE INVENTION

Surprisingly, it has been found that the monoclonal antibodies according to the invention exhibit high protective capacity against abscess formation. Prevention of abscess formation has been shown in a mouse-kidney model by administration of an alpha-toxin specific human monoclonal antibody according to the invention. Based on the nature of the toxin, namely being a secreted protein rather than a cell wall associated component (polysaccharide), any direct bactericidal effect, e.g. killing of the bacterial cell, or indirect immune system related effector function, such as complement mediated opsonophagocytosis, can be ruled out and does not account for the lack of abscess formation.

The term "monoclonal antibody" as used herein encompasses any partially or fully human monoclonal antibody independent of the source from which the monoclonal antibody is obtained. A fully human monoclonal antibody is preferred. The production of the monoclonal antibody by a hybridoma is preferred. The hybridoma may be a mammalian hybridoma, such as murine, cattle or human. A preferred hybridoma is of human origin. The monoclonal antibody may also be obtained by genetic engineering and in particular CDR grafting of the CDR segments as defined in the claims onto available monoclonal antibodies by replacing the CDR regions of the background antibody with the specific CDR segments as defined in the claims.

The term "CDR region" means the complementarity determining region of an antibody, i.e. the region determining the specificity of an antibody for a particular antigen. Three CDR regions (CDR1 to CDR3) on both the light and heavy chain are responsible for antigen binding.

The positions of the CDR regions within the heavy chain are as follows:

CDR1 region amino acids 26 to 33 within the $V_H$ exon,
CDR2 region amino acids 51 to 58 within the $V_H$ exon,
CDR3 region amino acids 97 to 110 within the $V_H$ exon.

The positions of the CDR regions are independent from the class of antibody, i.e. IgM, IgA of IgG.

The positions of the CDR region within the lambda type light chain are as follows:
CDR1 region amino acids 26 to 33 within the Vλ exon,
CDR2 region amino acids 51 to 53 within the Vλ exon,
CDR3 region amino acids 90 to 101 within the Vλ exon.

Amino acid alignments of the $V_H$, $V_X$ and $V_\lambda$ exon can be obtained from V Base database http://imgt dot cines dot fr/IMGT low dash vquest/share/textes/).

The term "fragment" means any fragment of the antibody capable of binding to the alpha-toxin of S. aureus. The fragment has a length of at least 10, preferably 20, more preferably 50 amino acids. It is further preferred that the fragment comprises the binding region of the antibody. It is preferred that the fragment is a Fab, $F(ab')_2$, single chain or domain antibody. Most preferred is a Fab or $F(ab')_2$ fragment or a mixture thereof. Antibody fragments may be glycosylated, for example containing carbohydrate moieties in the antibody variable regions.

Accordingly, the present invention further provides a monoclonal antibody as defined herein, wherein the antibody is a Fab, $F(ab')_2$, single chain or domain antibody fragment.

The term "mutein" encompasses any muteins of the monoclonal antibody differing by the addition, deletion, and/or substitution of at least one amino acid. Preferably, the mutein of the monoclonal antibody carries at least one conservative substitution in any of the CDR's in the heavy chain and/or light chain as indicated in the claims. More preferably, the mutein has not more than 5, not more than 4, preferably not more than 3, particularly preferred not more than 2 conservative substitutions. The capacity of the fragment or mutein of the antibody to be capable of binding to the alpha-toxin of *S. aureus* is determined by direct ELISA as described in the Example section: the purified alpha-toxin is immobilized on the solid phase of ELISA plates. Antibody fragments or muteins of the antibodies are incubated with the immobilized alpha-toxin, and bound antibodies or muteins thereof are visualized by a suitable enzyme-conjugated secondary antibody.

The term "conservative substitution" means a replacement of one amino acid belonging to a particular physico-chemical group with an amino acid belonging to the same physico-chemical group. The physico-chemical groups are defined as follows:

The physico-chemical group of non-polar amino acids comprises: glycine, alanine, valine, leucine, isoleucine, methionine, proline, phenylalanine, and tryptophan. The group of amino acids having uncharged polar side chains comprises asparagine, glutamine, tyrosine, cysteine, and cystine. The physico-chemical group of amino acids having a positively charged polar side chain comprises lysine, arginine, and histidine. The physico-chemical group of amino acids having a negatively charged polar side chain comprises aspartic acid and glutamic acid, with their carboxylate anions also referred to as aspartate and glutamate.

According to a further embodiment, the present invention provides a monoclonal antibody specific for alpha-toxin of *S. aureus*, wherein the variable region of the light chain of the antibody has the amino acid sequence of SEQ ID NO:7 and the variable region of the heavy chain has the amino acid sequence of SEQ ID NO:8, or a fragment thereof capable of binding alpha-toxin of *S. aureus*, or a variant of said antibody capable of binding alpha-toxin of *S. aureus*, wherein the amino acid sequence of the variable region of the light chain of the antibody is at least 85% identical to SEQ ID NO:7 and the amino acid sequence of the variable region of the heavy chain of the antibody is at least 85% identical to SEQ ID NO:8.

The term "variant" as used herein refers to a polypeptide, wherein the amino acid sequence exhibits a certain degree of identity with the amino acid sequence as set forth in the sequence listing.

The term "% identity" known to the person skilled in the art designates the degree of relatedness between two or more polypeptide molecules, which is determined by the agreement between the sequences. The percentage of "identity" is found from the percentage of identical regions in two or more sequences, taking account of gaps or other sequence features.

The percentage of identity of mutually related polypeptides can be determined by means of known procedures. As a rule, special computer programs with algorithms taking account of the special requirements are used. Preferred procedures for the determination of identity firstly generate the greatest agreement between the sequences studied. Computer programs for the determination of the identity between two sequences include, but are not limited to, the GCG program package, including GAP (Devereux J et al., (1984); Genetics Computer Group University of Wisconsin, Madison (Wis.); BLASTP, BLASTN and FASTA (Altschul S et al., (1990)). The BLAST X program can be obtained from the National Centre for Biotechnology Information (NCBI) and from other sources (BLAST Handbook, Altschul S et al., NCB NLM NIH Bethesda Md. 20894; Altschul S et al., 1990). The well-known Smith Waterman algorithm can also be used for the determination of percentage of identity.

Preferred parameters for the sequence comparison include the following:

| | |
|---|---|
| Algorithm: | Needleman S. B. and Wunsch, C. D. (1970) |
| Comparison matrix: | BLOSUM62 from Henikoff S. and Henikoff J. G. (1992) |
| Gap penalty: | 12 |
| Gap-length penalty: | 2 |

The GAP program is also suitable for use with the above parameters. The above parameters are the standard parameters (default parameters) for amino acid sequence comparisons, in which gaps at the ends do not decrease the identity value. With very small sequences compared to the reference sequence, it can further be necessary to increase the expectancy value to up to 100,000 and in some cases to reduce the word length (word size) to down to 2.

Further model algorithms, gap opening penalties, gap extension penalties and comparison matrices including those named in the Program Handbook, Wisconsin Package, Version 9, September 1997, can be used. The choice will depend on the comparison to be performed and further on whether the comparison is performed between sequence pairs, where GAP or Best Fit are preferred, or between one sequence and a large sequence database, where FASTA or BLAST are preferred. An agreement of 85% determined with the aforesaid algorithms is described as 85% identity. The same applies for higher degrees of identity.

In preferred embodiments, the variants according to the invention have an identity of 85% or more, preferably 90% or more, and more preferably 95% or more.

According to a preferred embodiment of the present invention, the monoclonal antibody is a human antibody. The term "human" as used herein means that the human monoclonal antibody is substantially free of amino acid sequences of foreign species, preferably the human monoclonal antibody consists entirely of human amino acid sequence.

The light chain of the monoclonal antibody according to the present invention can be of the kappa or lambda type.

In a preferred embodiment of the invention, the light chain is of the lambda type. The light chain may be either a naturally occurring chain including a naturally rearranged, a genetically modified or synthetic type of light chain.

The heavy chain of the monoclonal antibody of the present invention may be selected from the isotypes IgM, IgA, or IgG, preferably IgG.

According to a further preferred embodiment of the invention, the heavy chain of the monoclonal antibody is of the IgG type.

The term "capable of binding" as used herein refers to the binding which occurs between an antibody and its recognized antigen to which the antibody was produced. This type of binding is specific binding in contrast to non-specific which occurs in the absence of the antigen.

Antibodies capable of binding the alpha-toxin are prepared using a hybridoma technology, wherein the B-cell is a mammalian B-cell, such as murine, cattle or human. Preferably the B-cell is a human B-cell. Alternatively, the monoclonal antibody capable of binding alpha-toxin may be obtained by CDR grafting of the CDR regions as indicated in the claims onto available monoclonal antibodies thereby producing a monoclonal antibody specific for alpha-toxin of S. aureus in accordance with the present invention.

In a further embodiment of the invention, a monoclonal antibody capable of binding alpha-toxin of S. aureus is provided, which is obtainable from a mammalian B-cell, such as murine, cattle or human, preferably a human B cell or a hybridoma obtained by fusion of said human B cell with a myeloma or heteromyeloma cell.

In a further embodiment the invention provides a hybridoma capable of producing the monoclonal antibody capable of binding alpha-toxin of S. aureus as defined herein.

The term "alpha-toxin" as used herein refers to a bacterial protein produced by S. aureus. The alpha-toxin undergoes oligomerization into a heptameric pre-pore after binding to the cell surface of the host cell. The formation of the pore is a leading cause of apoptosis and cell lysis. The capability of the monoclonal antibody to bind to both the monomeric and oligomeric forms of S. aureus derived alpha-toxin is therefore of fundamental importance for a potent protection.

According to a further preferred embodiment of the invention the monoclonal antibody of the invention is capable of specifically binding monomeric and oligomeric forms of alpha-toxin of S. aureus. According to a further embodiment of the invention the monoclonal antibody of the invention or fragment or mutein thereof is capable of specifically binding either monomeric or oligomeric forms of alpha-toxin of S. aureus or both of them.

The term "oligomeric form" as used herein includes a form other than the monomeric form of alpha-toxin, such as dimeric, trimeric, tetrameric, pentameric, hexameric, heptameric etc or polymeric forms, such as the heptameric pre-pore form of alpha-toxin.

According to a further preferred embodiment, the monoclonal antibody of the invention is N-terminally, internally or C-terminally modified. The modifications include the di-, oligo-, or polymerization of the monomeric form e.g. by cross-linking using dicyclohexylcarbodiimide. The thus produced di-, oligo-, or polymers can be separated from each other by gel filtration. Further modifications include side chain modifications, e.g. modifications of ε-amino-lysine residues, or amino and carboxy-terminal modifications, respectively. Further modifications include post-translational modifications, e.g. glycosylation and/or partial or complete deglycosylation of the protein, and disulfide bond formation. The antibody may also be conjugated to a label, such as an enzymatic, fluorescent or radioactive label. Preferably, the modification is selected from at least one of oligomerization, glycosylation or conjugation to a drug or a label.

Further, the present invention provides nucleic acids encoding the heavy chain and light chain, respectively, of the monoclonal antibody of the present invention. The nucleic acid may be a naturally occurring nucleic acid either derived from the germ line or from rearrangement occurring in B-cells, alternatively the nucleic acids may be synthetic. Synthetic nucleic acids also include nucleic acids having modified internucleoside bonds including phosphothioester to increase resistance of the nucleic acids from degradation. The nucleic acid may be genetically engineered or completely synthetically produced by nucleotide synthesis.

The present invention further provides vectors comprising at least one nucleic acid encoding the light chain of the monoclonal antibody of the present invention and/or at least one nucleic acid encoding the heavy chain of the monoclonal antibody of the present invention. The nucleic acids may be either present in the same vector or may be present in the form of binary vectors. The vector preferably comprises the promoter operatively linked to the nucleic acid in order to facilitate expression of the nucleic acid encoding the light and/or heavy chain. Preferably, the vector also includes an origin for replication and maintenance in a host cell. The vector may also comprise a nucleotide sequence encoding a signal sequence located 5' of the nucleic acid encoding the light chain or heavy chain. The signal sequence may facilitate secretion of the encoded chain into the medium.

Preferably, the vector is derived from adenoviruses, vaccinia viruses, baculoviruses, SV 40 viruses, retroviruses, plant viruses or bacteriophages such as lambda derivatives or M13. The particularly preferred vector is a vector containing the constant regions of human Ig heavy chains and human light chains, such as the integrated vector system for eukaryotic expression of immunoglobulins described by Persic et al., 1987.

Further, the present invention provides host cells comprising the vector and/or the nucleic acid suitable for the expression of the vector. In the art numerous prokaryotic and eukaryotic expression systems are known wherein eukaryotic host cells such as yeast cells, insect cells, plant cells and mammalian cells, such as HEK293-cells, PerC6-cells, CHO-cells, COS-cells or HELA-cells and derivatives thereof are preferred. Particularly preferred are human production cell lines. It is preferred that the transfected host cells secrete the produced antibody into the culture medium. If intracellular expression is achieved, then renaturation is performed in accordance with standard procedures such as e.g. those described by Benetti et al., 1998.

The human monoclonal antibodies according to the invention are generated from blood lymphocytes of a convalescent patient and thus result in naturally refined and selected antibodies with high affinity for neutralization and effective protection against infections.

The present invention also provides methods for producing the monoclonal antibody. In one embodiment, the monoclonal antibody is produced by culturing the above-described hybridoma. The produced monoclonal antibody is secreted into the supernatant and can be purified from it by applying conventional chromatographic techniques.

Alternatively, the monoclonal antibody is produced by the host cell comprising a vector according to the present invention and culturing the host cell under conditions suitable for recombinant expression of the encoded antibody chain. Preferably, the host cell comprises at least one nucleic acid encoding the light chain and at least one nucleic acid encoding the heavy chain and is capable of assembling the monoclonal antibody such that a 3-dimensional structure is generated which is equivalent to the 3-dimensional structure of a monoclonal antibody produced by a mammalian, preferably human B-cell. If the light chain is produced separately from the heavy chain, then both chains may be purified and subsequently be assembled to produce a monoclonal antibody having essentially the 3-dimensional structure of a monoclonal antibody as produced by a mammalian, preferably human B-cell.

The monoclonal antibody may also be obtained by recombinant expression of the encoded light and/or heavy chain wherein the nucleic acid is produced by isolating a nucleic acid encoding a monoclonal antibody in a known manner and grafting of the nucleic acid sequence encoding the CDR's as defined in the claims onto the isolated nucleic acid.

The present invention further provides pharmaceutical compositions comprising at least one monoclonal antibody and/or at least one nucleic acid encoding a light and/or heavy chain of the monoclonal antibody.

The pharmaceutical composition may further comprise antibiotic drugs such as streptomycin, penicillin and vancomycin etc, preferably coupled to the monoclonal antibody of the invention.

The pharmaceutical compositions comprise the monoclonal antibody in a dosage range of 0.1-100 mg/kg body weight.

The pharmaceutical compositions may be administered in any known manner such as intravenous, intra-muscular, intra-dermal, subcutaneous, intra-peritoneal, topical, intra-nasal administration, or as inhalation spray.

In a preferred embodiment of the invention the pharmaceutical compositions are used for the prophylaxis or treatment of abscess formation in an organ of a mammalian patient, such as cattle, pig, cats, dogs, horses, human. In a preferred embodiment of the invention the pharmaceutical compositions are applied to human patients. In a further embodiment of the invention the abscess formation is caused by an *S. aureus* infection. Further, the *S. aureus* infection to be treated with the pharmaceutical composition of the invention may be for example an infection of the breast, such as mastitis.

Accordingly, the present invention provides the use of a monoclonal antibody or the nucleic acid encoding the variable region of the light chain and/or the heavy chain as defined herein for the preparation of a pharmaceutical composition for prophylaxis or treatment of an abscess formation in an organ in a mammalian, preferably human patient.

In a preferred embodiment of the invention the pharmaceutical compositions, the monoclonal antibody or the nucleic acid encoding the variable region of the light chain or the heavy chain as defined herein is applied for prophylaxis or treatment of an abscess formation in an organ, such as kidney, heart, liver, gallbladder, pancreas, small intestine, large intestine, lung, brain, skin, eye, lymphatic tissue or spleen. In a preferred embodiment of the invention, the abscess to be treated is an abdominal abscess. Accordingly, the abdominal organ to be treated is liver, gallbladder, spleen, pancreas, small intestine, kidneys, and large intestine.

The term "abscess formation" as used herein refers to the formation of an abscess in an organ, such as kidney, heart, liver, gallbladder, pancreas, small intestine, large intestine, lung, brain, skin, eye, lymphatic tissue or spleen. The term "abscess" as used herein means a collection of pus that has accumulated in a cavity formed by the tissue on the basis of an infectious process (usually caused by bacteria or parasites). The toxins released by these multiplying bacteria destroy cells and trigger an inflammatory response, which draws large numbers of white blood cells to the area and increases the regional blood flow. These leukocytes break down the dead tissues and absorb the bacteria by means of phagocytosis. Thick green or yellowish pus is formed from the broken-down tissues, the dead bacteria and leukocytes, and the extracellular fluid that has accumulated. An abscess is characterized by encapsulation by an abscess wall that is formed by the adjacent healthy cells in an attempt to keep the pus from infecting neighboring structures. It is a defensive reaction of the tissue to prevent the spread of infectious materials to other parts of the body. Abscesses may occur in any kind of solid tissue but most frequently on skin surface (where they may be superficial pustules (boils) or deep skin abscesses), in the lungs, brain, kidneys and tonsils. Major complications are spreading of the abscess material, such as organ seeding to adjacent or remote tissues and extensive regional tissue death (gangrene). Abscess formation is detected by evaluating the bacterial load within the organ.

The term "abdominal abscess" as used herein refers to an abscess in an organ of the abdominal cavity. The abdominal cavity is the body cavity that holds the bulk of the viscera and which is located below (or inferior to) the thoracic cavity, and above the pelvic cavity. It is a part of the abdominopelvic cavity. Organs of the abdominal cavity include the stomach, liver, gallbladder, spleen, pancreas, small intestine, kidneys, and large intestine.

"Organ seeding" as used herein means the dissemination of live bacteria from the local site of infection to distant tissues and organs. Organ seeding is characterized by the presence of live infecting bacterial cells in healthy tissue without formation of encapsulated macroscopic colonies of bacterial cells.

"Bacterial load" as used herein is defined as the amount of live bacterial cells within a well defined anatomical tissue expressed as the amount of bacterial cells growing out to colonies on solid growth media, such as agar plates. For the purpose of evaluating the bacterial load within an organ, the organ is surgically extracted from surrounding tissue and the organ tissue is meshed up under sterile conditions in sterile saline solution to destroy the well structured organization of the tissue and to separate bacterial cells from the mammalian tissue. A defined amount of cell suspension (or serial dilutions thereof in sterile saline) is spread on solid bacterial growth media. Bacterial load is expressed as "colony forming units" per kidney (e.g. cfu/kidney).

The present invention also provides a test kit for the diagnosis of *S. aureus* infections comprising at least one monoclonal antibody of the present invention and optionally further suitable ingredients for carrying out a diagnostic test.

Ingredients suitable for carrying out a diagnostic test are for example a buffer solution with an osmolality within a range of 280-320 mOsm/Liter and a pH value within a range of pH 6-8; a buffer solution containing chelating agents; a buffer solution containing monovalent or bivalent cations with the total cation concentration of the buffer composition ranging from about 0.02 M to about 2.0 M; and/or a buffer solution containing animal or human derived serum at a concentration between 0.01% and 20%.

The test kit is suitable for the specific reliable diagnosis of a *S. aureus* infection. A test assay may be based on a conventional ELISA test in liquid or membrane-bound form. The detection may be direct or indirect as known in the art wherein the antibody is optionally conjugated to an enzymatic, fluorescent or radioactive label.

Accordingly, the present invention also provides the use of at least one monoclonal antibody according to the invention for detecting binding to alpha-toxin in a sample. Binding of the antibody according to the invention to alpha-toxin can be detected for example with HRP-conjugated goat anti human IgG secondary antibody.

BRIEF DESCRIPTION OF THE FIGURES

FIG. 1 shows the DNA and amino acid sequence of the human monoclonal antibody 243-4 heavy chain variable region (DNA sequence—SEQ ID NO:24; amino acid sequence—SEQ ID NO:25). The CDR1 region of 243-4 is at positions 26 to 33, the CDR2 region of 243-4 is at positions 51 to 58, and the CDR3 region of 243-4 is at positions 97 to 110.

FIG. 2 shows the DNA and amino acid sequence of the human monoclonal antibody 243-4 light chain variable region (DNA sequence—SEQ ID NO:26 amino acid sequence—SEQ ID NO:27). The CDR1 region of 243-4 is at positions 26 to 33, the CDR2 region of 243-4 is at positions 51 to 53, and the CDR3 region of 243-4 is at positions 90 to 101.

In FIG. 4, M means size marker, numbers 1-12 are epidemic S. aureus strains and αTox is a purified alpha-toxin.

Figure 3:
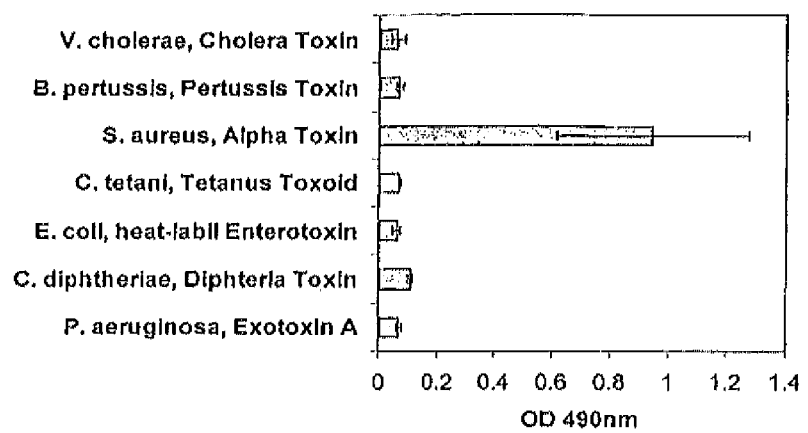
FIG. 3 shows the antigen specificity of human monoclonal antibody 243-4. Antigen specificity of antibody 243-4 was evaluated by binding to a panel of bacterial toxins in an ELISA assay. ELISA was performed on microtiter plates coated with purified toxins. After overnight incubation at room temperature the microtiter plates were blocked with BSA and binding of mAb 243-4 to immobilized toxins was detected with HRP-conjugated goat anti human IgG secondary antibody. Binding of human monoclonal antibody 243-4 to S. aureus alpha-toxin is clearly favored over binding to all other toxins tested.

The following examples illustrate the invention but are not intended to limit the scope of the present invention. Further embodiments will be apparent for the person skilled in the art when studying the specification and having regard to common general knowledge.

EXAMPLES

Example 1

DNA and Amino Acid Sequences of 243-4

The antibody specificity is determined by the DNA- and amino acid-sequence, respectively. DNA sequences of the variable fragments of the heavy and light chains were determined. For RNA isolation 5×10e5 hybridoma cells were pelleted by centrifugation and homogenized using Qiashredder columns (#79654, Qiagen). The mRNA was then isolated from homogenized hybridoma cell pellets by using the RNeasy-Kit (#74124, Qiagen) according to the instruction handbook of the supplier. Built on isolated mRNA, cDNA was synthesized by reverse transcription using Superscript II reverse transcriptase (#18064-022, Invitrogen). Genes of antibody 243-4 were amplified from synthesized cDNA using the Advantage 2 PCR Kit (#639206, Clontech) according to the instruction handbook of the supplier. Specific amplification of antibody genes was guaranteed by application of primer combinations designed for the amplification of human rearranged IgG variable region genes (Welschof et at, 1995). For amplification of both the variable heavy chain domains (VH) and the variable light chain domains (VL) a set of chain-specific forward primers was used in combination with one backward primer that specifically anneals in the constant domains of either the heavy chain or the light chain (VH amplification CH IgG in combination with VH1, VH2, and VH3; VL amplification CL λ in combination with VL λ 1, VL λ 2/5, VL ? 3, VL A 4a, VL λ 4b, and VL λ 6; see Table 1). PCR amplificates were then cloned in the plasmid pCR4-TOPO of the TOPO TA Cloning Kit for Sequencing (#K457540, Invitrogen) and purified plasmid DNA was finally sent in for sequencing (Microsynth, Balgach, Switzerland) using the plasmid specific primers of the TOPO Cloning Kit (T3 and T7, see Table 1). The DNA sequences obtained were processed and aligned using the clone manager software package (#87S-501-1787, Scientific&Educational Software). Resulting from the performed alignments a consensus sequence was defined and subsequently analyzed using the V Base database of all human germline variable region sequences (http://imgt dot cines dot fr/IMGT low dash vguestishare/textes/). Based on the initial sequencing results additional chain-specific internal primer sequences (VL-atox as and VH-atox as, see Table 1) were designed and applied in order to confirm the identified antibody sequence in the annealing regions of the primer combinations that were used before. The thereby generated antibody genes were applied to sequencing as described above, as shown in FIGS. 1 and 2.

coated with purified toxins at a concentration of 1 µg/ml each. After overnight incubation at room temperature the microtiter plates were blocked for 2 h with 0.5% BSA and binding of mAb 243-4 (1 µg/ml) to immobilized toxins was detected with HRP-conjugated goat anti human IgG secondary antibody at 1:2000 dilution (#62-8420, Zymed Laboratories, Invitrogen). Reactions were stopped with HCl.

Optical density was read on an ELISA reader at 490 nm using Softmax Pro® software, as shown in FIG. 3.

TABLE 1

Primer sequences used for amplification and sequencing of variable domains of antibody 243-4

| Primer | Source | SEQ ID NO | Sequence (5'-3') | Application |
|---|---|---|---|---|
| CH IgG | Welschof et al., J Immunol Met, 179, 1995 | 9 | GAC C(G$^{50}$)GA TGG GCC CTT GGT GGA* | PCR, sequencing |
| VH1 | | 10 | C(G$^{50}$)AG GTG CAG CTG GTG CAG TGT* | PCR, sequencing |
| VH2 | | 11 | CAG GTG(A$^{50}$) CAG CTG CAG G(C$^{50}$)AG TC* | PCR, sequencing |
| VH3 | | 12 | GAG GTG CAG CTG G(T$^{50}$)TG GAG TCT* | PCR, sequencing |
| CL λ | | 13 | AGA GGA G(C$^{50}$)GG GAA CAG AGT GAC* | PCR, sequencing |
| VLλ 1 | | 14 | CAG TCT GTG T(C$^{50}$)TG ACG(T$^{50}$) CAG CCG CCC TCA* | PCR, sequencing |
| VLλ 2/5 | | 15 | CAG TCT GCG CTG ACT CAA(G$^{50}$) CCG G(C$^{50}$)CC TCT* | PCR, sequencing |
| VLλ 3 | | 16 | TCC TAT GAA CTG ACT CAG CCA CCC(T$^{50}$) T | PCR, sequencing |
| VLλ 4a | | 17 | TCT GAA CTG ACT CAG CCG(A$^{33}$T$^{33}$) C(G$^{50}$)CC TC* | PCR, sequencing |
| VLλ 4b | | 18 | TCT GAA CTG ACT CAG GAC CCT GC(T$^{50}$)T* | PCR, sequencing |
| VLλ 6 | | 19 | A(G$^{50}$)AT TTT ATG CTG ACT CAG CCC CAC TCT* | PCR, sequencing |
| T3 | #K457540 | 20 | ATT AAC CCT CAC TAA AGG GA | Sequencing |
| T7 | Invitrogen | 21 | TAA TAC GAC TCA CTA TAG GG | Sequencing |
| VL-atox as | Internal design | 22 | AGG CTG TCA TCC CAT GTT GCA CAG | PCR, sequencing |
| VH-atox as | | 23 | CTG CTG CTC CCA GAT CGT CTC GC | PCR, sequencing |

*Bases in parentheses represent substitutions at the previous position and the number indicates the percentage at which the nucleotides are substituted.

Example 2

Antigen Specificity of Human Monoclonal Antibody 243-4 (ELISA)

Antigen specificity of antibody 243-4 was evaluated by binding to a panel of bacterial toxins (alpha-toxin: #120, List Biological Laboratories; all other toxins: in house production, Kenta Biotech AG) in an ELISA assay. ELISA was performed on microtiter plates (#439454, Nunc MaxiSorp)

Example 3

Binding to Alpha-Toxin of Epidemic S. aureus Strains in Western Blot Experiments Alpha-toxin production from twelve epidemic S. aureus strains was monitored after 16 h of growth in BHI media (#255003, Becton Dickinson) at 37° C. The strains were obtained from the German S. aureus reference center (Robert Koch Institute, Wernigerode) and represent the most prevalent epidemic strains currently causing *S. aureus* infections. Some of these strains produce less alpha-toxin compared to others resulting in different signal strength.

Figure 4:
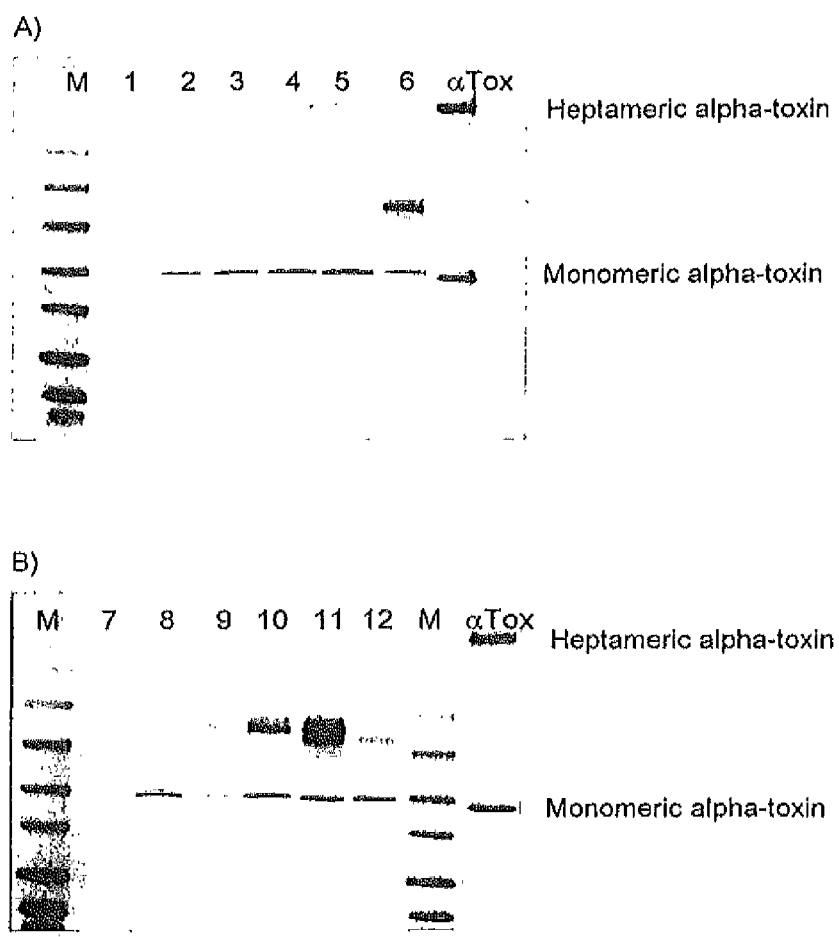
FIG. 4 shows the binding of human monoclonal antibody 243-4 to alpha-toxin of epidemic S. aureus strains in Western Blot experiments. Alpha-toxin production of twelve epidemic S. aureus strains was monitored from bacterial cultures at stationary growth phase. After cultivation normalized bacterial supernatants and purified alpha-toxin were loaded on a SDS-PAGE gel and applied to electroblotting. After blocking the nitrocellulose membrane was incubated with purified human monoclonal antibody 243-4. Production and recognition of both monomeric and/or heptameric alpha-toxin from every evaluated epidemic strain was proven by binding of human monoclonal antibody 243-4.

The different genotypes of the evaluated strains are depicted in Table 2. After cultivation bacteria were pelleted by centrifugation and culture supernatants were normalized to $OD_{600}=0.6$ of the initial bacterial cultures. 25 μl of each supernatant was loaded on a 4-20% SDS-PAGE gel (#EC60252, Invitrogen) followed by electroblotting for 1 h. One μg of purified alpha-toxin (#120, List Biological Laboratories) was loaded and blotted in parallel as reference. After blocking with 5% milk powder for 1 h, the nitrocellulose membrane (#LC2000, Invitrogen) was incubated with 50 μg/ml of purified human monoclonal antibody 243-4. Binding of antibody 243-4 to alpha-toxin was finally detected with HRP-conjugated goat anti human IgG secondary antibody at 1:2000 dilution (#62-8420, Zymed Laboratories, Invitrogen, as shown in FIG. 4.

TABLE 2

Panel of hospital and community acquired Methicillin resistant *S. aureus* strains (MRSA) of representative clonal lines

| Western Blot designation | Robert Koch Institute isolate number | MLST type*[1] | CC*[2] | Spa sequence type*[3] |
|---|---|---|---|---|
| 1 | 93-00134 | ST247 | 8 | t051 |
| 2 | 06-00842 | ST8 | 8 | t008 |
| 3 | 06-02222 | ST9 | 8 | t008 |
| 4 | 06-01579 | ST239 | 8 | t031 |
| 5 | 06-00219 | ST5 | 5 | t002 |
| 6 | 06-00409 | ST225 | 5 | t003 |
| 7 | 06-01019 | ST45 | 45 | t1384 |
| 8 | 06-02182 | ST22 | 22 | t965 |
| 9 | 03-02773 | ST1 | 1 | t175 |
| 10 | 06-00373 | ST8 | 8 | t008 |
| 11 | 05-01089 | ST22 | 22 | t310 |
| 12 | 06-00300 | ST80 | 80 | t044 |

*[1]Multi locus sequence typing
*[2]Clonal complex
*[3]Analysis of the protein A gene (spa) variable repeat region Example 4

Affinity Determination (by BIAcore)

Figure 5:
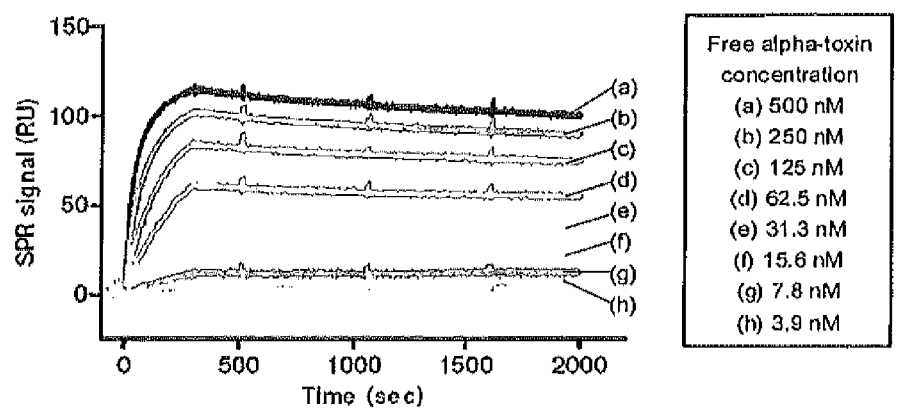
FIG. 5 shows the affinity determination of human monoclonal antibody 243-4 by BIAcore. The binding kinetics of human monoclonal antibody 243-4 was analyzed using a BIAcore 2000 instrument. Different alpha-toxin concentrations were applied to a flow cell immobilized with mAb 243-4. Association and dissociation phases were recorded to calculate the dissociation constant of the antibody. The kinetic data were evaluated by global fitting using the software BIAevaluation 4.1.

Surface plasmon resonance was measured using a BIAcore 2000 instrument (BIAcore). All experiments were performed in 20 mM Mops buffer, pH 7.0, 150 mM NaCl, and 0.1 mg/ml BSA. First, goat anti human IgG (#81-7100, Zymed Laboratories, Invitrogen) was immobilized on a CM5 chip (BIAcore) to approximately 13200 RU by amine-coupling as described in the BIAapplications handbook. In addition to the initial covalent coating the antibody 243-4 was bound to the sensor chip via interaction with the preimmobilized anti human IgG antibody, finally yielding an additional immobilization level of approximately 240 RU. For kinetic characterization of the antigen-antibody interaction pulses of increasing alpha-toxin concentrations (3.9 nM, 7.8 nM, 15.62 nM, 31.25 nM, 62.5 nM, 125 nM, 250 nM, and 500 nM; #120, List Biological Laboratories) were injected at a flow rate of 50 μl/min. After each measurement cycle (5 min of association followed by 30 min of dissociation) the antibody-antigen complex was resolved by regeneration of the surface with 10 mM glycine-HCl at pH 1.7. For calculation of the dissociation constant of antibody 243-4 the association and dissociation phases were recorded and evaluated by global fitting using the software BIAevaluation 4.1 (BIAcore AB, as shown in FIG. 5). For global fit analysis only these antigen concentrations were taken into account, which allowed the analysis following the Langmuir 1:1 binding model 125 nM, Table 2) and as outlined in the BIAcore manual.

TABLE 3

Kinetic constants of the quantitative alpha-toxin - antibody 243-4 interaction

| Antigen concentration | $k_{ass}$ (l mol$^{-1}$ s$^{-1}$) | $K_{diss}$ (s$^{-1}$) | $K_D$ (in M) |
|---|---|---|---|
| 3.9 nM | $5.7 * 10^4$ | $8.2 * 10^{-5}$ | $1.4 * 10^{-9}$ |
| 7.8 nM | $6.1 * 10^4$ | $1.0 * 10^{-5}$ | $1.6 * 10^{-9}$ |
| 15.62 nM | $6.2 * 10^4$ | $8.0 * 10^{-5}$ | $1.3 * 10^{-9}$ |
| 31.25 nM | $6.3 * 10^4$ | $9.7 * 10^{-5}$ | $1.5 * 10^{-9}$ |
| 62.5 nM | $6.6 * 10^4$ | $9.0 * 10^{-5}$ | $1.4 * 10^{-9}$ |
| 125 nM | $6.2 * 10^4$ | $8.9 * 10^{-5}$ | $1.4 * 10^{-9}$ |
| Mean value | $6.2 * 10^4 \pm 0.3 * 10^4$ | $8.9 * 10^{-5} \pm 0.7 * 10^{-5}$ | $1.4 * 10^{-9} \pm 0.1 * 10^{-9}$ |

Example 5

Tissue Culture Model of Human Alveolar Cell Injury

Figure 6:
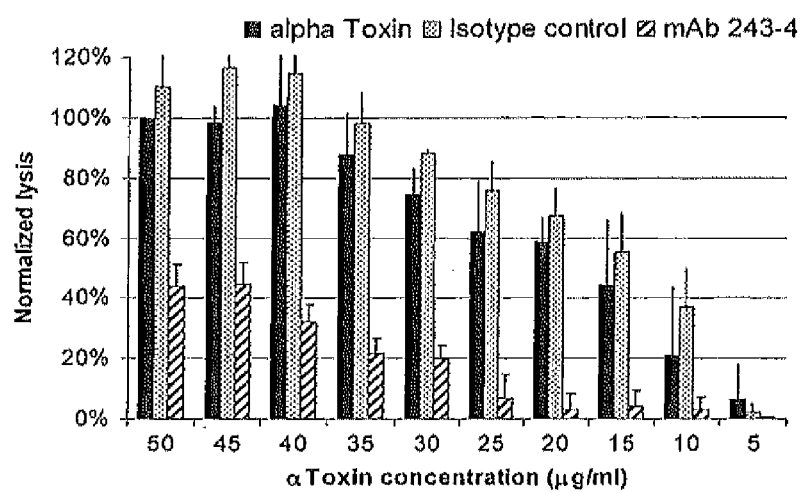
FIG. 6 shows the alpha-toxin neutralization by human monoclonal antibody 243-4 in a tissue culture model of human alveolar cell injury. Human A549 alveolar epithelial cells were cocultured for 16 h with alpha-toxin in the presence of either isotype control antibody or monoclonal antibody 243-4. After that time the cells were analyzed by the lactate dehydrogenase (LDH) assay, which provides a readout of cellular injury caused by alpha-toxin and reveals the degree of protection that can be achieved with the applied antibodies. For interpretation of results the degree of cell lysis, which was resulting from preincubation with the highest alpha-toxin concentration was set to 100%. Cells treated with toxin only showed a titration of lysis in dependence of the applied alpha-toxin concentration. The same titration was observed when alpha-toxin was preincubated with the isotype control antibody, indicating no protective effect of the isotype control. In contrast, human alveolar epithelial cells were protected from alpha-toxin dependent lysis by incubation with human monoclonal antibody 243-4. The experiment was performed on three independent occasions, each of which confirmed the protectivity of the antibody 243-4.

Human A549 alveolar epithelial cells were plated in RPMI media (#R0883, Sigma-Aldrich) at a density of 3×10e5 cells per well. In parallel increasing concentrations of alpha-toxin (5 μg/ml-50 μg/ml; #120, List Biological Laboratories) were preincubated with media only, 20 μg/ml of isotype control antibody (human IgG1 lambda, purified myeloma protein; #I 5029, Sigma-Aldrich) or 20 μg/ml of purified monoclonal antibody 243-4. After 4 h of incubation at 37° C., alpha-toxin or alpha-toxin-antibody solutions were added to the cells and incubation was proceeded for additional 16 h. After that time the cells were analyzed by the lactate dehydrogenase (LDH) assay (#04744934001, Roche), which provides a readout for cellular LDH release into the culture media, as shown in FIG. 6.

Example 6

Mouse Model of Multiorgan Infection

Figure 7:
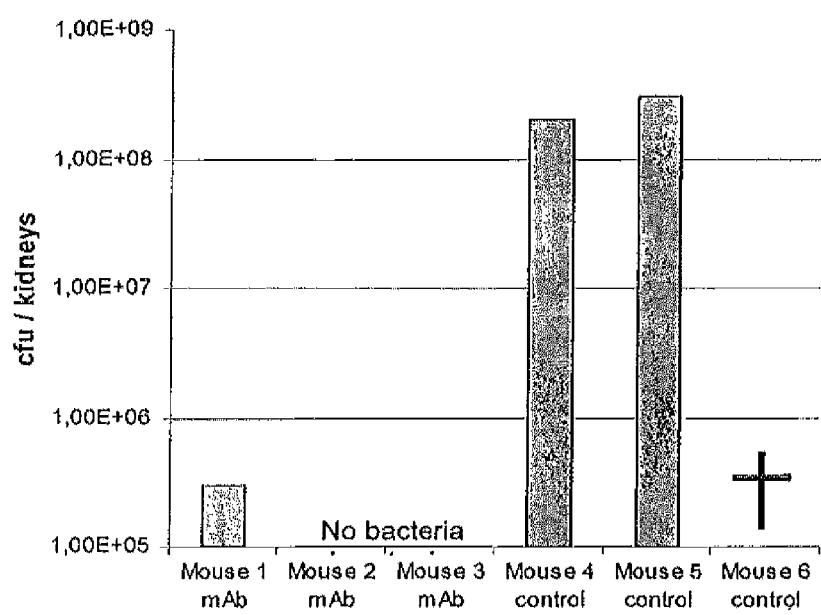
FIG. 7 shows the protective effect of human monoclonal antibody 243-4 in a central venous catheter related mouse model of multiorgan infection. Twenty-four hours after catheter placement, the mice received 1×10e7 CFU of S. aureus strain US300 and either 7.5 mg/kg of mAb 243-4 or PBS via the catheter. Two days later, mice of the treatment group received a second antibody dose (5 mg/kg), while mice of the control group received PBS only. Five days after surgery mice were euthanized to monitor kidney bacterial load and kidney abscess formation. Mice immunized with monoclonal antibody 243-4 showed a strong reduction of bacterial load and no kidney abscess formation was observed, while all control mice possessed a high bacterial kidney load and a strong abscess formation.

Female Balb/c mice (Charles River, Sulzfeld, Germany), weighing 27-31 g were acclimated for 14 days prior to surgery. The mice were obtained from the supplier specified as pathogen free. For placement of the catheter the mice were intraperitoneally anesthetized with xylazin (8 mg/kg body weight)/ketamine (100 mg/kg body weight). A minimal horizontal skin incision was made at the left side of the shaved neck in order to place the single lumen polyethylene catheter (outer diameter 0.6 mm, Föhr Medical Instruments, Seeheim, Germany) in the superior vena cava. Twenty-four hours after catheter placement, the mice received 1×10e7 CFU of *S. aureus* strain US300 (in 100 μl) and either 7.5 mg/kg of purified mAb 243-4 or PBS (in 50 μl) via the catheter. Two days later, mice of the treatment group received a second antibody dose (5 mg/kg), while mice of the control group received PBS only. Five days after surgery mice were euthanized to monitor kidney bacterial load and kidney abscess formation. For that reason kidneys were aseptically harvested from euthanized animals and homogenized in saline. Before organ withdrawal the location of the catheter in the superior vena cave was confirmed and prior to kidney homogenization the organs were examined for abscess formation macroscopically. Finally, serial dilutions of the organ homogenates were cultured on MPK plates for at least 48 h at 37° C. Colony forming units (CFU) were calculated and documented as CFU/kidney, as shown in FIG. 7.

TABLE 4

Differential kidney abscess formation in treatment and control group animals

| | | |
|---|---|---|
| MAb Treatment group | Mouse 1 | No abscess formation in both kidneys |
| | Mouse 2 | No abscess formation in both kidneys |
| | Mouse 3 | No abscess formation in both kidneys |
| Control group | Mouse 4 | Strong abscess formation in both kidneys |
| | Mouse 5 | Strong abscess formation in both kidneys |
| | Mouse 6 | Not determined as mouse died before end of experiment |

REFERENCES

Adlam C. et al., 1977: Effect of Immunization with Highly purified Alpha- and Beta-Toxins on *Staphylococcal* Mastitis in Rabbits.
Infect and Immun. 17: 250-256.
Altschul S. et al., 1990: Basic local alignment search tool. J. Mol. Biol. 215: 403.
Benetti P. H. et al., 1998: Expression and characterization of the recombinant catalytic subunit of casein kinase II from the yeast Yarrowia lipolytica in *Escherichia coli*.
Protein Expr Purif (13):283-290.
Corbin B. D. et al., 2008: Metal Chelation and Inhibition of Bacterial Growth in Tissue Abscesses
Science 319,962-965.
DeLeo F. R. and Otto M., 2008: An antidote for *Staphylococcus aureus* pneumonia. J Exp Med 05(2): 271-274.
Devereux J et al., 1984: A comprehensive set of sequence analysis programs for the VAX Nucleic Acids Research 12 (12): 387.
Goode R. L., Baldwin J. N., 1974: Comparison of purified alpha-toxins from various strains of *Staphylococcus aureus*.
Appl Microbiol. 28(1):86-90.
Henikoff S. and Henikoff J. G., 1992: Amino acid substitution matrices from protein blocks.
Proc Natl Acad Sci USA. 1992 Nov. 15; 89(22):10915-9.
Heveker N. et al., 1994a: A human monoclonal antibody with the capacity to neutralize *Staphylococcus aureus* alpha-toxin. Hum. Antibod. Hybridomas 5: 18-24.
Heveker N. et al., 1994b: Characterization of Neutralizing monoclonal Antibodies directed against *Staphylococcus aureus* alpha-toxin. Hybridoma 13: 263-270.
Kapral F. A. et al., 1980. Formation of Intraperitoneal Abscesses by *Staphylococcus aureus*.
Infect and Immun. 30: 204-211.
Kielian T. et al., 2001: Diminished Virulence of an Alpha-Toxin Mutant of *Staphylococcus aureus* in Experimental Brain Abscesses; Infect and Immun. (69), 6902-6911.
Levine M M. et al., 1983: New Knowledge on Pathogenesis of Bacterial Enteric Infections as Applied to Vaccine Development.
Microbiol. Reviews (47), 510-550.
McElroy M C et al., 1999: Alpha-toxin damages the air-blood barrier of the lung in a rat model of *Staphylococcus aureus* induced pneumonia. Infect and Immun 67, 5541-5544.
Needleman S. B. Wunsch C. D., 1970: A general method applicable to the search for similarities in the amino acid sequence of two proteins.
J. Mol. Biol. 48: 443.
Persic L. et al., 1997: An integrated vector system for the eukaryotic expression of antibodies or their fragments after selection from phage display libraries.
Gene 10; 187(1):9-18.
Schwan W. R. et al., 2003: Loss of hemolysin expression in *Staphylococcus aureus* agr mutant correlates with selective survival during mixed infections in murine abscesses and wounds. FEMS Imm and Med Microbiol 28, 23-28.
Tzianabos A. O. et al., 2001: Structural rationale for the modulation of abscess formation by *Staphylococcus aureus* capsular polysaccharides. PNAS 98: 9365-9370.
Von Köckrick-Blickwede M. et al., 2008: Immunological Mechanisms Underlying the Genetic Predisposition to Severe *Staphylococcus aureus* Infection in the Mouse Model.
The American Journal of Pathology 173 (6), 1657-1668.
Wardenburg, J. B., and Schneewind O. 2008: Vaccine protection against *Staphylococcus aureus* pneumonia. J. Exp. Med. 205:287.-294.
Wardenburg, J. B. et al., 2007: Poring over pores: alpha-hemolysin and Panton-Valentine leukocidin in *Staphylococcus aureus* pneumonia. Nat. Med. 13:1405-1406.
Welschof M. et al.; 1995: Amino acid sequence based PCR primers for amplification of rearranged human heavy and light chain immunoglobulin variable region genes.
J Immunol Methods. 179(2):203-14.
WO2007/145689 Use of Alpha-Toxin for treating and preventing *Staphylococcus* infections.

The invention claimed is:

1. A monoclonal antibody or binding fragment thereof specific for alpha-toxin of *S. aureus*,
   wherein the variable region of the light chain of the antibody comprises the amino acid sequence of SEQ ID NO: 27 and the variable region of the heavy chain comprises the amino acid sequence of SEQ ID NO: 8;
   wherein the antibody binding fragment is a Fab, F(ab')2, single chain or domain antibody, and
   wherein the antibody or the binding fragment specifically binds to alpha-toxin of *S. aureus*.

2. The monoclonal antibody or fragment of claim 1, wherein the antibody is a human antibody.

3. The monoclonal antibody or fragment of claim 1, wherein the light chain is of the lambda type.

4. The monoclonal antibody or fragment of claim 1, wherein the heavy chain is of the IgG type.

5. The monoclonal antibody or fragment of claim 1, wherein the antibody specifically binds monomeric and oligomeric forms of alpha-toxin of *S. aureus*.

6. The monoclonal antibody or fragment of claim 1, wherein the antibody is N-terminally, internally or C-terminally modified and the modification is at least one selected from the group consisting of oligomerization, glycosylation and conjugation to a drug or a label.

7. The monoclonal antibody of claim 1 obtainable from a mammalian B cell or a hybridoma obtained by fusion of the mammalian B cell with a myeloma or heteromyeloma cell.

8. A hybridoma capable of producing the monoclonal antibody of claim 1.

9. A method of producing the monoclonal antibody of claim 1, the method comprising culturing a hybridoma capable of producing said monoclonal antibody under conditions allowing for secretion of an antibody.

10. A pharmaceutical composition comprising at least one monoclonal antibody or fragment of claim 1, and a pharmaceutically acceptable carrier or ingredient.

11. A method of treating an abscess or promoting abscess formation prophylaxis in an organ, comprising administering to the organ a monoclonal antibody of claim 1.

12. The method of claim 11, wherein the abscess in an organ is an abdominal abscess.

13. The method of claim 11, wherein the organ is kidney, heart, liver, lung, brain, skin or spleen.

14. The method of claim 11, wherein the abscess formation is caused by an *S. aureus* infection.

15. A test kit for diagnosis of an *S. aureus* infection in a sample comprising at least one monoclonal antibody or fragment of claim 1.

16. A monoclonal antibody specific for alpha-toxin of *S. aureus*, wherein the variable region of the light chain of the antibody comprises SEQ ID NO: 1 in the CDR1 region, SEQ ID NO: 2 in the CDR2 region and SEQ ID NO: 3 in the CDR3 region, and
   wherein the variable region of the heavy chain of the antibody comprises SEQ ID NO: 4 in the CDR1 region, SEQ ID NO: 5 in the CDR2 region and SEQ ID NO: 6 in the CDR3 region, and wherein the antibody specifically binds to alpha-toxin of *S. aureus*.

17. The fragment of claim 1, wherein the fragment is a Fab or F(ab')2.

* * * * *

SEQUENCE LISTING

```
<160> NUMBER OF SEQ ID NOS: 27

<210> SEQ ID NO 1
<211> LENGTH: 8
<212> TYPE: PRT
<213> ORGANISM: Homo sapiens
<220> FEATURE:
<221> NAME/KEY: MISC_FEATURE
<223> OTHER INFORMATION: CDR1 light chain

<400> SEQUENCE: 1

Ser Ser Asn Ile Gly Ser Asn Thr
1               5

<210> SEQ ID NO 2
<211> LENGTH: 3
```

```
<212> TYPE: PRT
<213> ORGANISM: Homo sapiens
<220> FEATURE:
<221> NAME/KEY: MISC_FEATURE
<223> OTHER INFORMATION: CDR2 light chain

<400> SEQUENCE: 2

Thr Asn Asn
1

<210> SEQ ID NO 3
<211> LENGTH: 12
<212> TYPE: PRT
<213> ORGANISM: Homo sapiens
<220> FEATURE:
<221> NAME/KEY: MISC_FEATURE
<223> OTHER INFORMATION: CDR3 light chain

<400> SEQUENCE: 3

Ala Thr Trp Asp Asp Ser Leu Asn Gly Leu Tyr Val
1               5                   10

<210> SEQ ID NO 4
<211> LENGTH: 8
<212> TYPE: PRT
<213> ORGANISM: Homo sapiens
<220> FEATURE:
<221> NAME/KEY: MISC_FEATURE
<223> OTHER INFORMATION: CDR1 heavy chain

<400> SEQUENCE: 4

Gly Tyr Lys Phe Gly Thr His Trp
1               5

<210> SEQ ID NO 5
<211> LENGTH: 8
<212> TYPE: PRT
<213> ORGANISM: Homo sapiens
<220> FEATURE:
<221> NAME/KEY: MISC_FEATURE
<223> OTHER INFORMATION: CDR2 heavy chain

<400> SEQUENCE: 5

Ile His Pro Ala Asp Ser Glu Thr
1               5

<210> SEQ ID NO 6
<211> LENGTH: 14
<212> TYPE: PRT
<213> ORGANISM: Homo sapiens
<220> FEATURE:
<221> NAME/KEY: MISC_FEATURE
<223> OTHER INFORMATION: CDR3 heavy chain

<400> SEQUENCE: 6

Ala Arg Arg Ser Gly Ser Ser Ser Trp Tyr Ala Leu Asp Phe
1               5                   10

<210> SEQ ID NO 7
<211> LENGTH: 123
<212> TYPE: PRT
<213> ORGANISM: Homo sapiens
<220> FEATURE:
<221> NAME/KEY: MISC_FEATURE
<223> OTHER INFORMATION: variable region light chain

<400> SEQUENCE: 7

Gln Ser Val Leu Thr Gln Ser Pro Ser Ala Ser Gly Thr Pro Gly Gln
```

```
            1               5                  10                 15
          Arg Val Thr Ile Ser Cys Ser Gly Gly Ser Ser Asn Ile Gly Ser Asn
                          20                 25                 30

Thr Val Asn Trp Tyr Gln Gln Phe Pro Gly Ala Ala Pro Lys Leu Leu
                          35                 40                 45

Ile Tyr Thr Asn Asn Gln Arg Pro Ser Gly Val Pro Asp Arg Phe Ser
                  50                 55                 60

Gly Ser Lys Ser Gly Thr Ser Ala Ser Leu Ala Ile Ser Gly Leu Gln
          65                 70                 75                 80

Ser Glu Asp Glu Ala Asp Tyr Tyr Cys Ala Thr Trp Asp Asp Ser Leu
                          85                 90                 95

Asn Gly Leu Tyr Val Phe Gly Thr Gly Thr Lys Val Thr Val Leu Gly
                          100                105                110

Gln Pro Lys Ala Asn Pro Ile Val Thr Leu Phe
                          115                120
```

<210> SEQ ID NO 8
<211> LENGTH: 129
<212> TYPE: PRT
<213> ORGANISM: Homo sapiens
<220> FEATURE:
<221> NAME/KEY: MISC_FEATURE
<223> OTHER INFORMATION: variable region heavy chain

<400> SEQUENCE: 8

```
          Glu Val Gln Met Val Gln Ser Gly Ala Glu Val Lys Lys Pro Gly Glu
          1               5                  10                 15

Pro Leu Lys Ile Ser Cys Lys Gly Ser Gly Tyr Lys Phe Gly Thr His
                          20                 25                 30

Trp Ile Gly Trp Val Arg Gln Arg Pro Gly Lys Gly Leu Glu Trp Met
                          35                 40                 45

Gly Ile Ile His Pro Ala Asp Ser Glu Thr Lys Tyr Ser Pro Ser Phe
                  50                 55                 60

Gln Gly Gln Val Ser Phe Ser Ala Asp Lys Ser Ser Asn Thr Ala Tyr
          65                 70                 75                 80

Leu His Trp Ser Thr Leu Arg Ala Ser Asp Thr Ala Met Tyr Tyr Cys
                          85                 90                 95

Ala Arg Arg Ser Gly Ser Ser Trp Tyr Ala Leu Asp Phe Trp Gly
                          100                105                110

Gln Gly Thr Met Val Thr Val Ser Ser Ala Ser Thr Lys Gly Pro Ser
                          115                120                125

Val
```

<210> SEQ ID NO 9
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (4)..(4)
<223> OTHER INFORMATION: 50% C, 50% G

<400> SEQUENCE: 9
gacngatggg cccttggtgg a                                               21

<210> SEQ ID NO 10
<211> LENGTH: 21

```
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(1)
<223> OTHER INFORMATION: 50%C, 50%G
<220> FEATURE:
<221> NAME/KEY: misc_feature
<222> LOCATION: (1)..(1)
<223> OTHER INFORMATION: 50% C, 50% G

<400> SEQUENCE: 10
naggtgcagc tggtgcagtc t                                              21

<210> SEQ ID NO 11
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (6)..(6)
<223> OTHER INFORMATION: 50% G, 50% A
<220> FEATURE:
<221> NAME/KEY: misc_feature
<222> LOCATION: (16)..(16)
<223> OTHER INFORMATION: 50% G, 50% C

<400> SEQUENCE: 11
caggtncagc tgcagnagtc                                                20

<210> SEQ ID NO 12
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (13)..(13)
<223> OTHER INFORMATION: 50%G, 50% T
<220> FEATURE:
<221> NAME/KEY: misc_feature
<222> LOCATION: (13)..(13)
<223> OTHER INFORMATION: 50% G, 50% T

<400> SEQUENCE: 12
gaggtgcagc tgntggagtc t                                              21

<210> SEQ ID NO 13
<211> LENGTH: 21
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (7)..(7)
<223> OTHER INFORMATION: 50%G, 50%C

<400> SEQUENCE: 13
agagganggg aacagagtga c                                              21

<210> SEQ ID NO 14
<211> LENGTH: 27
<212> TYPE: DNA
<213> ORGANISM: Artificial Sequence
<220> FEATURE:
```

```
<223> OTHER INFORMATION: PCR primer
<220> FEATURE:
<221> NAME/KEY: misc_feature
<222> LOCATION: (10)..(10)
<223> OTHER INFORMATION: 50% T, 50% C
<220> FEATURE:
<221> NAME/KEY: misc_feature
<222> LOCATION: (15)..(15)
<223> OTHER INFORMATION: 50% G, 50% T

<400> SEQUENCE: 14
cagtctgtgn tgacncagcc gccctca                                              27

<210> SEQ ID NO 15
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (18)..(18)
<223> OTHER INFORMATION: 50% A, 50% G
<220> FEATURE:
<221> NAME/KEY: misc_feature
<222> LOCATION: (22)..(22)
<223> OTHER INFORMATION: 50% G, 50% C

<400> SEQUENCE: 15
cagtctgcgc tgactcancc gncctct                                              27

<210> SEQ ID NO 16
<211> LENGTH: 25
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (24)..(24)
<223> OTHER INFORMATION: 50% C, 50% T

<400> SEQUENCE: 16
tcctatgaac tgactcagcc accnt                                                25

<210> SEQ ID NO 17
<211> LENGTH: 23
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (18)..(18)
<223> OTHER INFORMATION: 33.3% G, 33.3% A, 33.3% T
<220> FEATURE:
<221> NAME/KEY: misc_feature
<222> LOCATION: (19)..(19)
<223> OTHER INFORMATION: 50% C, 50% G

<400> SEQUENCE: 17
tctgaactga ctcagccnnc ctc                                                  23

<210> SEQ ID NO 18
<211> LENGTH: 24
<212> TYPE: DNA
<213> ORGANISM: Artificial Sequence
<220> FEATURE:
<223> OTHER INFORMATION: PCR primer
<220> FEATURE:
<221> NAME/KEY: misc_feature
```

```
<222> LOCATION: (23)..(23)
<223> OTHER INFORMATION: 50% C, 50% T

<400> SEQUENCE: 18
tctgaactga ctcaggaccc tgnt                                          24

<210> SEQ ID NO 19
<211> LENGTH: 27
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(1)
<223> OTHER INFORMATION: 50% A, 50% G

<400> SEQUENCE: 19
nattttatgc tgactcagcc ccactct                                       27

<210> SEQ ID NO 20
<211> LENGTH: 20
<212> TYPE: DNA
<213> ORGANISM: Artificial Sequence
<220> FEATURE:
<223> OTHER INFORMATION: sequencing primer

<400> SEQUENCE: 20
attaaccctc actaaaggga                                               20

<210> SEQ ID NO 21
<211> LENGTH: 20
<212> TYPE: DNA
<213> ORGANISM: Artificial Sequence
<220> FEATURE:
<223> OTHER INFORMATION: sequencing primer

<400> SEQUENCE: 21
taatacgact cactataggg                                               20

<210> SEQ ID NO 22
<211> LENGTH: 24
<212> TYPE: DNA
<213> ORGANISM: Artificial Sequence
<220> FEATURE:
<223> OTHER INFORMATION: PCR primer

<400> SEQUENCE: 22
aggctgtcat cccatgttgc acag                                          24

<210> SEQ ID NO 23
<211> LENGTH: 23
<212> TYPE: DNA
<213> ORGANISM: Artificial Sequence
<220> FEATURE:
<223> OTHER INFORMATION: PCR primer

<400> SEQUENCE: 23
ctgctgctcc cagatcgtct cgc                                           23

<210> SEQ ID NO 24
<211> LENGTH: 387
<212> TYPE: DNA
<213> ORGANISM: Homo sapiens
<220> FEATURE:
<221> NAME/KEY: misc_feature
<223> OTHER INFORMATION: VH
```

<400> SEQUENCE: 24

```
gaggtgcaga tggtgcagtc tggagcagag gtgaaaaagc cgggggaacc tctgaagatc    60
tcctgtaagg gttctggata caagtttggc acccactgga tcggctgggt gcgccagagg   120
cccgggaaag gcctggagtg gatgggaatc atccatcctg ctgactctga aaccaagtac   180
agcccgtcat tccaaggcca ggtctctttc tcagccgaca agtccagcaa taccgcctac   240
ctacattgga gcaccctgag ggcctcggac accgccatgt attactgtgc gagacgatct   300
gggagcagca gttggtatgc tcttgatttc tggggccaag gacaatggt caccgtctct   360
tcagcctcca ccaagggccc atccgtc                                       387
```

<210> SEQ ID NO 25
<211> LENGTH: 129
<212> TYPE: PRT
<213> ORGANISM: Homo sapiens
<220> FEATURE:
<221> NAME/KEY: misc_feature
<223> OTHER INFORMATION: VH

<400> SEQUENCE: 25

```
Glu Val Gln Met Val Gln Ser Gly Ala Glu Val Lys Lys Pro Gly Glu
1               5                   10                  15
Pro Leu Lys Ile Ser Cys Lys Gly Ser Gly Tyr Lys Phe Gly Thr His
            20                  25                  30
Trp Ile Gly Trp Val Arg Gln Arg Pro Gly Lys Gly Leu Glu Trp Met
        35                  40                  45
Gly Ile Ile His Pro Ala Asp Ser Glu Thr Lys Tyr Ser Pro Ser Phe
    50                  55                  60
Gln Gly Gln Val Ser Phe Ser Ala Asp Lys Ser Ser Asn Thr Ala Tyr
65                  70                  75                  80
Leu His Trp Ser Thr Leu Arg Ala Ser Asp Thr Ala Met Tyr Tyr Cys
                85                  90                  95
Ala Arg Arg Ser Gly Ser Ser Ser Trp Tyr Ala Leu Asp Phe Trp Gly
            100                 105                 110
Gln Gly Thr Met Val Thr Val Ser Ser Ala Ser Thr Lys Gly Pro Ser
        115                 120                 125
Val
```

<210> SEQ ID NO 26
<211> LENGTH: 369
<212> TYPE: DNA
<213> ORGANISM: Homo sapiens
<220> FEATURE:
<221> NAME/KEY: misc_feature
<223> OTHER INFORMATION: VL

<400> SEQUENCE: 26

```
cagtctgtgc tgactcagtc accctcagcg tcgggaccc cgggcagag ggtcaccatc     60
tcttgttctg gaggcagctc caacatcgga agtaatactg taaattggta ccaacagttc   120
ccaggagcgg cccccaaact cctcatctat actaataatc agcggccctc aggggtccct   180
gaccgattct ctggctccaa gtctggcacc tcagcctccc tggccatcag tgggctccag   240
tctgaggatg aggctgatta ttactgtgca acatgggatg acagcctaaa tggcctttac   300
gtcttcggaa ctgggaccaa ggtcaccgtc ctaggtcagc ccaaggccaa ccccactgtc   360
actctgttc                                                           369
```

```
<210> SEQ ID NO 27
<211> LENGTH: 123
<212> TYPE: PRT
<213> ORGANISM: Homo sapiens
<220> FEATURE:
<221> NAME/KEY: misc_feature
<223> OTHER INFORMATION: VL

<400> SEQUENCE: 27

Gln Ser Val Leu Thr Gln Ser Pro Ser Ala Ser Gly Thr Pro Gly Gln
1               5                   10                  15

Arg Val Thr Ile Ser Cys Ser Gly Gly Ser Ser Asn Ile Gly Ser Asn
                20                  25                  30

Thr Val Asn Trp Tyr Gln Gln Phe Pro Gly Ala Ala Pro Lys Leu Leu
            35                  40                  45

Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65              70                  75                  80

Ser Glu Asp Glu Ala Asp Tyr Tyr Cys Ala Thr Trp Asp Asp Ser Leu
                85                  90                  95

Asn Gly Leu Tyr Val Phe Gly Thr Gly Thr Lys Val Thr Val Leu Gly
            100                 105                 110

Gln Pro Lys Ala Asn Pro Thr Val Thr Leu Phe
            115                 120
```